United States Patent [19]

Eidenschink et al.

[11] Patent Number: 4,755,323
[45] Date of Patent: Jul. 5, 1988

[54] LIQUID-CRYSTALLINE DIELECTRICS

[75] Inventors: Rudolf Eidenschink, Münster; Georg Weber, Erzhausen, both of Fed. Rep. of Germany

[73] Assignee: Merck Patent Gesellschaft mit beschrankter Haftung, Darmstadt, Fed. Rep. of Germany

[21] Appl. No.: 839,293

[22] Filed: Mar. 13, 1986

Related U.S. Application Data

[63] Continuation of Ser. No. 624,172, Jun. 25, 1984, abandoned.

[30] Foreign Application Priority Data

Jun. 25, 1983 [DE] Fed. Rep. of Germany ....... 3322982

[51] Int. Cl.[4] .............. C09K 19/34; G02F 1/13; C07D 405/00; C07D 409/00; C07D 411/00
[52] U.S. Cl. ............... 252/299.61; 252/299.5; 350/350 R; 350/350 S; 544/295; 544/296; 544/315; 544/316; 544/242; 544/318; 544/333; 544/334; 544/335; 546/187; 546/195; 546/209; 546/210; 549/370; 549/377; 549/378; 549/379; 549/380
[58] Field of Search .............. 549/370, 377, 378, 379, 549/380; 544/296, 295, 315, 316, 318, 333, 334, 335, 242; 252/299.5, 299.61; 350/350 R, 350 S; 546/187, 195, 210, 209

[56] References Cited

U.S. PATENT DOCUMENTS

| 4,200,580 | 4/1980 | Hsu | 252/299.61 |
| 4,298,528 | 11/1981 | Sethofer | 252/299.61 |
| 4,313,878 | 2/1982 | Hsu | 252/299.61 |
| 4,322,354 | 3/1982 | Sorkin | 252/299.61 |
| 4,325,830 | 4/1982 | Sethofer | 252/299.61 |
| 4,344,856 | 8/1982 | Demus et al. | 252/299.61 |
| 4,348,324 | 9/1982 | Demus et al. | 252/299.61 |
| 4,450,094 | 5/1984 | Sato et al. | 252/299.61 |
| 4,486,332 | 12/1984 | Demus et al. | 252/299.61 |
| 4,510,069 | 4/1985 | Eidenschink et al. | 252/299.61 |
| 4,512,636 | 4/1985 | Andrews et al. | 252/299.61 |
| 4,521,327 | 6/1985 | Demus et al. | 252/299.61 |
| 4,537,698 | 8/1985 | Sucron et al. | 252/299.61 |
| 4,564,694 | 1/1986 | Hirai et al. | 252/299.5 |
| 4,597,892 | 7/1986 | Zaschke et al. | 252/299.61 |
| 4,617,140 | 10/1982 | Eidenschink et al. | 252/299.61 |
| 4,632,515 | 12/1986 | Gray et al. | 252/299.5 |

FOREIGN PATENT DOCUMENTS

| 56501 | 7/1982 | European Pat. Off. | 252/299.61 |
| 87679 | 9/1983 | European Pat. Off. | 252/299.61 |
| 2092169 | 8/1982 | Fed. Rep. of Germany | 252/299.61 |
| 3328638 | 2/1985 | Fed. Rep. of Germany | 252/299.61 |
| 3335244 | 4/1985 | Fed. Rep. of Germany | 252/299.61 |
| 3405914 | 8/1985 | Fed. Rep. of Germany | 252/299.61 |
| 3411571 | 10/1985 | Fed. Rep. of Germany | 252/299.61 |
| 3437935 | 9/1986 | Fed. Rep. of Germany | 252/299.61 |
| 47-31714 | 8/1972 | Japan | 252/299.61 |
| 55-149372 | 11/1980 | Japan | 252/299.61 |
| 56-95183 | 8/1981 | Japan | 252/299.61 |
| 86/00067 | 1/1986 | PCT Int'l Appl. | 252/299.61 |

OTHER PUBLICATIONS

Karmysheva, L. A., et al., Advances in Liquid Crystal Res. & Appl., ed. L. Bata, Pergamon Press, Oxford (1980).

Zaschke, H., et al., Liquid Crystals & Ordered Fluids, vol. 4, pp. 75-87 (1984).

Primary Examiner—Teddy S. Gron
Attorney, Agent, or Firm—Millen & White

[57] ABSTRACT

New 1,4-dioxanes of the formula I

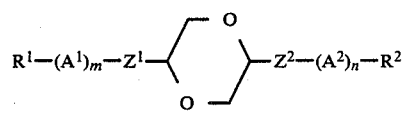

wherein
 $R^1$ and $R^2$ each signify and alkyl group with 1 - 10 C-atoms, wherein one or two $CH_2$ groups can also be replaced by O-atoms, F, Cl, Br or CN,
 $R^2$ also H,
 $A^1$ and $A^2$ each signify 1,4-phenylene, 1,4-cyclohexylene, 1,3-dioxane-2,5-diyl, 1,4-dioxane-2,5-diyl, peperidine-1,4-diyl, 1,4-bicyclo(2,2,2)-octylene or pyrimidine-2,5-diyl groups, unsubstituted or substituted by 1 - 4 F-atoms,
 $Z^1$ and $Z^2$ each signify —CO—O—, —O—CO—, $CH_2CH_2$—, $OCH_2$— —$CH_2O$— or a single bond,
 m and n each signify 0, 1, 2 or 3,
 (m+n), however, are at least 1 and at most 3,
 whereby for m=2 or 3, the groups $A^1$ and for n=2 or 3 the groups $A^2$ can each be the same or different from one another,
as well as the acid-addition salts of the basic ones of these compounds,
are suitable for use as components of liquid-crystalline dielectrics.

20 Claims, No Drawings

LIQUID-CRYSTALLINE DIELECTRICS

This application is a continuation application of U.S. Ser. No. 624,172, filed on June 25, 1984, now abandoned.

This invention relates to new 1,4-dioxanes useful as liquid crystalline compounds.

SUMMARY OF THE INVENTION

It is an object of the invention to provide new compounds having valuable liquid crystalline properties.

Upon further study of the specification and appended claims, further objects and advantages of this invention will become apparent to those skilled in the art.

These objects have been attained by providing new 1,4-dioxanes of the formula I

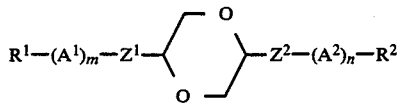

wherein $R^1$ and $R^2$ each signify an alkyl group with 1–10 C-atoms, wherein one or two $CH_2$ groups can also be replaced by 0-atoms, or signify F, Cl, Br or CN, $R^2$ also H $A^1$ and $A^2$ each signify 1,4-phenylene, 1,4-cyclohexylene, 1,3-dioxane-2,5-diyl, 1,4-dioxane-2,5-diyl, piperidine-1,4-diyl, 1,4-bicyclo(2,2,2)-octylene or pyrimidine-2,5-diyl groups unsubstituted or substituted by 1–4 F-atoms, $Z^1$ and $Z^2$ each signify -CO-O-, -O-CO-, $CH_2CH_2$-, $OCH_2$- or $-CH_2O$- or a single bond, m and n each signify 0, 1, 2 or 3

(m+n), however, are at least 1 and at most 3, whereby for m=2 or 3, the groups $A^1$ and for n=2 or 3 the groups $A^2$ can, in each case, be the same or different from one another, as well as the acid-addition salts of the basic ones of these compounds.

For the sake of simplicity, in the following "A" signifies the 1,4-dioxane-2,5-diyl group, "Phe" a 1,4-phenylene group, "Cy" a 1,4-cyclohexylene group, "Dio" a 1,3-dioxane-2,5-diyl group, "Bi" a bicyclo(2,2,2)-octylene group, "Pip" a piperidine-1,4-diyl group and "Pyr" a pyrimidine-2,5-diyl group, whereby these groups, especially the 1,4-phenylene group, can be unsubstituted or (except for A), can be substituted by 1–4 fluorine atoms.

DETAILED DISCUSSION

Similar compounds are known, e.g., from published European Patent Specification No. 19,665. However, in contradistinction to the present case, the there-given compounds contain no 1,4-dioxane rings.

The compounds of the formula I can, like similar compounds, be used as components of liquid-crystalline dielectrics, especially for displays, which depend upon the principle of the twisted cell, the guest-host effect, the effect of the deformation of aligned phases, the effect of dynamic scattering or the 2-frequency process.

The task forming the basis of the invention was to find new, stable, liquid-crystalline or mesogenic compounds which are suitable as components of liquid-crystalline dielectrics. It has been found that the compounds of formula I are outstandingly suitable as components of liquid-crystalline dielectrics. In particular, with their help, there can be produced stable, liquid-crystalline phases with strongly negative as well as positive dielectric anisotropy and thus small threshold or control voltage of electro-optical effects, very variable optical anisotropy and comparatively low viscosity.

Furthermore, with the making available of the compounds of formula I, there is, quite generally, considerably widened the palette of liquid-crystalline substances which, under various application-technical points of view, are suitable for the production of nematic mixtures.

The compounds of formula I possess a wide field of use. Depending upon the choice of substituents, these compounds can serve as basic materials from which liqud-crystalline dielectrics are preponderantly composed; however, compounds of formula I can also be added to liquid-crystalline basic materials of other classes of compounds in order, for example, substantially to influence the dielectric and/or optical anisotropy of such a dielectric. Furthermore, the compounds of formula I are suitable as intermediate products for the preparation of other substances which can be used as components of liquid-crystalline dielectrics.

In a pure state, the compounds of formula I are colorless and form liquid-crystalline mesophases in a temperature range which lies favorably for electro-optical use. They are very stable chemically, thermally and against light. They also provide polar substances in which highly polar additives, such as conductive salts and dichroitic dyestuffs, are readily soluble.

Thus, the subject of the invention are the compounds of formula I, as well as a process for their preparation, characterized in that one cyclizes a compound of the formula IIa or IIb

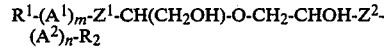

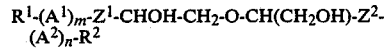

wherein $R^1$, $R^2$, $A^1$, $A^2$, $Z^1$, $Z^2$, m and n have the given meanings, or one of their reactive derivatives, or that, for the preparation of esters of the formula I (wherein $Z^1$ and/or $Z^2$ signifies -CO-O- or -O-CO-), one reacts a corresponding carboxylic acid or one of its reactive derivatives with a corresponding alcohol or one of its reactive derivatives, or that, for the preparation of 1,3-dioxane derivatives of the formula I (wherein $A^1$ and/or $A^2$ signifies 1,3-dioxane-2,5-diyl), one reacts a corresponding aldehyde with a corresponding diol, or that, for the preparation of nitriles of the formula I (wherein $R^1$ and/or $R^2$ signify CN), one dehydrates a corresponding carboxylic acid amide or reacts a corresponding carboxylic acid halide with sulphamide, or that, for the preparation of ethers of the formula I (wherein $R^1$ and/or $R^2$ signify alkyl chains, wherein one or two $CH_2$ groups are replaced by 0-atoms, and/or $Z^1$ and/or $Z^2$ are $-OCH_2$- or $-CH_2O$-), one etherifies a corresponding hydroxy compound, and/or that one possibly reacts a chlorine or bromine compound of the formula I (wherein $R^1$ and/or $R^2$ signify Cl or Br) with a cyanide, and/or that one possibly converts a base of the formula I into one of its acid-addition salts by treatment with an acid, or that one possibly liberates a compound of the formula I from one of its acid-addition salts by treatment with a base.

The subject of the invention is, furthermore, the use of the compounds of formula I as components of liquid-crystalline dielectrics. The subject of the invention are, furthermore, liquid-crystalline dielectrics with a content of at least one of the compounds of formula I, as well as electro-optical indicator elements which contain such dielectrics.

Above and subsequently, $R^1$, $R^2$, $A^1$, $A^2$, $Z^1$, $Z^2$, m and n have the given meaning insofar as nothing else is expressly stated.

The compounds of formula I consequently include compounds of the partial formulae Ia and Ib (each with two rings), Ic to Ie (each with three rings), as well as If to Ii (each with four rings):

| | |
|---|---|
| $R^1$-$A^1$-$Z^1$-A-$Z^2$-$R^2$ | Ia |
| $R^1$-$Z^1$-A-$Z^2$-$A^2$-$R^2$ | Ib |
| $R^1$-$(A^1)_2$-$Z^1$-A-$Z^2$-$R^2$ | Ic |
| $R^1$-$A^1$-$Z^1$-A-$Z^2$-$A^2$-$R^2$ | Id |
| $R^1$-$Z^1$-A-$Z^2$-$(A^2)_2$-$R^2$ | Ie |
| $R^1$-$(A^1)_3$-$Z^1$-A-$Z^2$-$R^2$ | If |
| $R^1$-$(A^1)_2$-$Z^1$-A-$Z^2$-$A^2$-$R^2$ | Ig |
| $R^1$-$A^1$-$Z^1$-A-$Z^2$-$(A^2)_2$-$R^2$ | Ih |
| $R^1$-$Z^1$-A-$Z^2$-$(A^2)_3$-$R^2$ | Ii. |

The preferred compounds of partial formulae Ia and Ib include those of partial formulae Iaa to Iaf, as well as Iba to Ibf:

| | |
|---|---|
| $R^1$-Phe-$Z^1$-A-$Z^2$-$R^2$ | Iaa |
| $R^1$-Cy-$Z^1$-A-$Z^2$-$R^2$ | Iab |
| $R^1$-Dio-$Z^1$-A-$Z^2$-$R^2$ | Iac |
| $R^1$-Pip-$Z^1$-A-$Z^2$-$R^2$ | Iad |
| $R^1$-Bi-$Z^1$-A-$Z^2$-$R^2$ | Iae |
| $R^1$-Pyr-$Z^1$-A-$Z^2$-$R^2$ | Iaf |
| $R^1$-$Z^1$-A-$Z^2$-Phe-$R^2$ | Iba |
| $R^1$-$Z^1$-A-$Z^2$-Cy-$R^2$ | Ibb |
| $R^1$-$Z^1$-A-$Z^2$-Dio-$R^2$ | Ibc |
| $R^1$-$Z^1$-A-$Z^2$-Pip-$R^2$ | Ibd |
| $R^1$-$Z^1$-A-$Z^2$-Bi-$R^2$ | Ibe |
| $R^1$-$Z^1$-A-$Z^2$-Pyr-$R^2$ | Ibf |

Among these, those of formula Iba are especially preferred.

Of the compounds of partial formulae Ic to Ii, those of partial formulae Ie and Ii are especially preferred, in detail those of partial formulae Ica to Iih:

| | |
|---|---|
| $R^1$-Phe-Phe-$Z^1$-A-$Z^2$-$R^2$ | Ica |
| $R^1$-Phe-Cy-$Z^1$-A-$Z^2$-$R^2$ | Icb |
| $R^1$-Cy-Phe-$Z^1$-A-$Z^2$-$R^2$ | Icc |
| $R^1$-Cy-Cy-$Z^1$-A-$Z^2$-$R^2$ | Icd |
| $R^1$-Phe-$Z^1$-A-$Z^2$-Phe-$R^2$ | Ida |
| $R^1$-Phe-$Z^1$-A-$Z^2$-Cy-$R^2$ | Idb |
| $R^1$-Cy-$Z^1$-A-$Z^2$-Phe-$R^2$ | Idc |
| $R^1$-Cy-$Z^1$-A-Z-Cy-$R^2$ | Idd |
| $R^1$-$Z^1$-A-$Z^2$-Phe-Phe-$R^2$ | Iea |
| $R^1$-$Z^1$-A-$Z^2$-Phe-Cy-$R^2$ | Ieb |
| $R^1$-$Z^1$-A-$Z^2$-Cy-Phe-$R^2$ | Iec |
| $R^1$-$Z^1$-A-$Z^2$-Cy-Cy-$R^2$ | Ied |
| $R^1$-Phe-Phe-Phe-$Z^1$-A-$Z^2$-$R^2$ | Ifa |
| $R^1$-Phe-Phe-Cy-$Z^1$-A-$Z^2$-$R^2$ | Ifb |
| $R^1$-Phe-Cy-Phe-$Z^1$-A-$Z^2$-$R^2$ | Ifc |
| $R^1$-Phe-Cy-Cy-$Z^1$-A-$Z^2$-$R^2$ | Ifd |
| $R^1$-Cy-Phe-Phe-$Z^1$-A-$Z^2$-$R^2$ | Ife |
| $R^1$-Cy-Phe-Cy-$Z^1$-A-$Z^2$-$R^2$ | Iff |
| $R^1$-Cy-Cy-Phe-$Z^1$A-$Z^2$-$R^2$ | Ifg |
| $R^1$-Cy-Cy-Cy-$Z^1$-A-$Z^2$-$R^2$ | Ifh |
| $R^1$-Phe-Phe-$Z^1$-A-$Z^2$-Phe-$R^2$ | Iga |
| $R^1$-Phe-Phe-$Z^1$-A-$Z^2$-Cy-$R^2$ | Igb |
| $R^1$-Phe-Cy-$Z^1$-A-$Z^2$-Phe $R^2$ | Igc |
| $R^1$-Phe-Cy-$Z^1$-A-$Z^2$-Cy-$R^2$ | Igd |
| $R^1$-Cy-Phe-$Z^1$-A-$Z^2$-Phe-$R^2$ | Ige |
| $R^1$-Cy-Phe-$Z^1$-A-$Z^2$-Cy-$R^2$ | Igf |
| $R^1$-Cy-Cy-$Z^1$-A-$Z^2$-Phe-$R^2$ | Igg |
| $R^1$-Cy-Cy-$Z^1$-A-$Z^2$-Cy-$R^2$ | Igh |
| $R^1$-Phe-$Z^1$-A-$Z^2$-Phe-Phe-$R^2$ | Iha |
| $R^1$-Phe-$Z^1$-A-$Z^2$-Phe-Cy-$R^2$ | Ihb |
| $R^1$-Phe-$Z^1$-A-$Z^2$-Cy-Phe-$R^2$ | Ihc |
| $R^1$-Phe-$Z^1$-A-$Z^2$-Cy-Cy-$R^2$ | Ihd |
| $R^1$-Cy-$Z^1$-A-$Z^2$-Phe-Phe-$R^2$ | Ihe |
| $R^1$-Cy-$Z^1$-A-$Z^2$-Phe-Cy-$R^2$ | Ihf |
| $R^1$-Cy-$Z^1$-A-$Z^2$-Cy-Phe-$R^2$ | Ihg |
| $R^1$-Cy-$Z^1$-A-$Z^2$-Cy-Cy-$R^2$ | Ihh |
| $R^1$-$Z^1$-A-$Z^2$-Phe-Phe-Phe-$R^2$ | Iia |
| $R^1$-$Z^1$-A-$Z^2$-Phe-Phe-Cy-$R^2$ | Iib |
| $R^1$-$Z^1$-A-$R^2$-Phe-Cy-Phe-$R^2$ | Iic |
| $R^1$-$Z^1$-A-$Z^2$-Phe-Cy-Cy-$R^2$ | Iid |
| $R^1$-$Z^1$-A-$Z^2$-Cy-Phe-Phe-$R^2$ | Iie |
| $R^1$-$Z^1$-A-$Z^2$-Cy-Phe-Cy-$R^2$ | Iif |

$R^1$-$Z^1$-A-$Z^2$-Cy-Cy-Phe-$R^2$      Iig $R^1$-$Z^1$-A-$Z^2$-Cy-Cy-Cy-$R^2$      Iih.

The compounds of the partial formulae Iea and Iib are especially preferred.

In the compounds of the above and subsequent formulae, $R^1$ and $R^2$ preferably signify alkyl, furthermore alkoxy (especially when these radicals stand on a Phe group) or another oxaalkyl group.

$A^1$ and $A^2$ are preferably Cy or Phe, furthermore preferably Dio or Pip; the compound of the formula I preferably contains not more than one of the radicals Dio, Pip, Bi or Pyr.

$Z^1$ and $Z^2$ are preferably single bonds, in the second place preferably -CO-O- or -O-CO- groups.

m is preferably 0, n is preferably 1.

In the compounds of the above and subsequent formulae, the alkyl radicals, in which also one ("alkoxy" or "oxaalkyl") or two ("alkoxyalkoxy" or "dioxaalkyl") $CH_2$ groups can also be replaced by O-atoms, are straight-chained or branched. They are preferably straight-chained, have 2, 3, 4, 5, 6 or 7 C-atoms and consequently preferably signify ethyl, propyl, butyl, pentyl, hexyl, heptyl, ethoxy, propoxy, butoxy, pentoxy, hexoxy, heptoxy, 2-oxapropyl (=methoxymethyl), 2-(=-ethoxymethyl) or 3-oxabutyl (=2-methoxyethyl), 2-, 3- or 4-oxapentyl, 2-, 3-, 4- or 5-oxahexyl, 2-, 3-, 4- 5- or 6-oxaheptyl, furthermore methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formula I, as well as Ia to Iih, with branched side groups $R^1$ or $R^2$ can sometimes, because of a better solubility in the usual liquid-crystalline base materials, be of importance but especially as chiral doping materials, if they are optically active. Branched groups of this kind contain, as a rule, not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

Among the compounds of the formulae I, as well as Ia to Iih, those are preferred in which at least one of the radicals contained therein has one of the given preferred meanings. Especially preferred smaller groups of compounds are those of the formulae Ij to Iq $R^1$-A-$Z^2$-$A^2$-$R^2$      Ij $R^1$-A-$A^2$-$R^2$      Ik $R_1$-A-Phe-$R^2$      Il $R^1$-A-Phe-CN      Im $R^1$-A-$(A^2)_2$-$R^2$      In $R^1$-A-Phe-Phe-$R^2$      Io $R^1$-A-$(A^2)_3$-$R^2$      Ip $R^1$-A-Phe-Phe-Cy-$R^2$      Iq Those of the above-mentioned formulae which contain one or more of the groups Dio, Pip and/or Pyr in each case include the two possible 2,5- and 1,4-positional isomers. Thus, for example, the partial formula Iac includes the 2-$R^1$-5-(A-$R^2$)-1,3-dioxanes and the 2(A-$R^2$)-5-$R^1$-1,3-dioxanes, the partial formula Iad the 1-$R^1$-4-(A-$R^2$)-piperidines and the 1-(A-$R^2$)-4-$R^1$-piperidines.

All the mentioned compounds which contain cyclohexane, 1,3-dioxane and/or 1,4-dioxane rings can be present as cis and as trans forms, as well as as mixtures.

Those compounds in which the substituents are in the trans-position to one another are preferred. As a rule, these are more stable; in many cases, the cis compounds (or mixtures) can be converted by treatment with a base, e.g. with a K tert.-butylate, in an inert solvent, such as dimethyl sulphoxide, into the trans compounds.

The compounds of the formula I are prepared by per se known methods such as are described in the literature (e.g. in standard works, such as HoubenWeyl, Methoden der Organischen Chemie, Georg-ThiemeVerlag, Stuttgart), namely under reaction conditions which are known and suitable for the said reactions. Use can thereby also be made of per se known variants which are here not mentioned in detail.

The starting materials can also, if desired, be formed in situ in such a manner that they are not isolated from the reaction mixture but rather immediately further reacted to give the compounds of the formula I.

The compounds of the formula I are obtained especially advantageously by cyclization of the compounds of the formulae IIa or IIb or of their reactive derivatives.

As a rule, the starting materials are new but can be prepared analogously to known materials with the help of per se known methods, e.g. by reaction of glycols of the formula $R^1$-$(A^1)_m$-$Z^1$-CHOH-$CH_2$OH and HO$CH_2$-CHOH-$Z^2$-$(A^2)_n$-$R^2$ or the corresponding halohydrins or epoxides. The compounds of the formulae IIa or IIb are preferably not isolated but rather only produced in situ.

Compounds of the formulae IIa or IIb, in which $R^1=R^2$, $A^1=A^2$, $Z^1=Z^2$ and m=n, can be obtained e.g. by dimerization of glycols of the formula $R^1$-$(A^1)_m$-$Z^1$-CHOH-$CH_2$OH or of the corresponding epoxides.

As reactive derivatives of the compounds of the formulae IIa or IIb, there are suitable e.g. the corresponding halogen derivatives (Hal in place of one or both OH groups); furthermore, corresponding reactive esters, e.g. alkyl or aryl sulphonates, wherein the alkyl groups contain especially 1–6, the aryl groups 6–10 C-atoms, e.g. the mono- or dimethane-, -benzene- or -p-toluenesulphonates of the mentioned diols.

As a rule, the cyclization takes place at temperatures between about 0° and 250° in the presence or absence of an inert solvent, e.g. of a hydrocarbon, such as benzene, toluene or xylene, of an amide, such as dimethylformamide, or of phosphoric acid hexamethyltriamide, of a sulphoxide, such as dimethyl sulphoxide, or of a ketone, such as acetone or acetophenone, expediently in the presence of an acid catalyst, e.g. of a mineral acid, such as sulphuric acid, hydrochloric acid, phosphoric acid, perchloric acid, of an organic sulphonic acid, such as benzene-, toluene- or naphthalene-sulphonic acid, of a Lewis acid, such as $BF_3$, $SnCl_4$ or $ZnCl_2$, or of an acid salt, such as $NaHSO_4$. In the case of the cyclization, there can also be used basic catalysts, e.g. alkali metal alcoholates, such as sodium or potassium methylate, ethylate or tert.-butylate, especially when, as derivatives of IIa or IIb, there are used corresponding halides, halogen alcoholates or esters.

Esters of the formula I ($Z^1$ and/or $Z^2$=-CO-O- or -O-CO-) can be obtained by esterification of corresponding carboxylic acids of the formulae $R^1$-$(A^1)_m$-COOH, $R^1$-$(A^1)_m$-$Z^1$-A-COOH, $R^2$-$(A^2)_n$-COOH or $R^2$-$(A^2)_n$-$Z^2$-A-COOH (or of their reactive derivatives) with alcohols or phenols of the formulae $R^2$-$(A^2)_n$-$Z^2$-A-OH, $R^2$-$(A^2)_n$-OH, $R^1$-$(A^1)_m$-$Z^1$-A-OH or $R^1$-$(A^1)_m$-OH (or their reactive derivatives).

As reactive derivatives of the said carboxylic acids, there are especially suitable the acid halides, above all the chlorides and bromides, furthermore the anhydrides, e.g. also mixed anhydrides of the formulae $R^1$-$(A^1)_m$-CO-O-COCH$_3$, $R^1$-$(A^1)_m$-$Z^1$-A-CO-O-COCH$_3$, $R^2$-$(A^2)_n$-CO-O-COCH$_3$ and $R^2$-$(A^2)_n$-$Z^2$-A-CO-O-COCH$_3$, azides or esters, especially alkyl esters with 1-4 C-atoms in the alkyl group.

As reactive derivatives of the said alcohols or phenols, there come into consideration especially the corresponding metal alcoholates or phenolates of the formulae $R^2$-$(A^2)_n$-$Z^2$-A-OM, $R^2$-$(A^2)_n$-OM, $R^1$-$(A^1)_m$-$Z^1$-A-OM and $R^1$-$(A^1)_m$-OM, wherein M signifies an equivalent of a metal, preferably of an alkali metal, such as Na or K.

The esterification is advantageously carried out in the presence of an inert solvent. Well suited are especially ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halohydrocarbons, such as carbon tetrachloride or tetrachloroethylene, and sulphoxides, such as dimethyl sulphoxide or sulpholane. Solvents not miscible with water can simultaneously be used advantageously for the azeotropic distilling off of the water formed by the esterification. Sometimes an excess of an organic base, e.g. pyridine, quinoline or triethylamine, can also be used as solvent for the esterification. The esterification can also be carried out in the absence of a solvent, e.g. by simple heating of the components in the presence of sodium acetate. The reaction temperature usually lies between $-50°$ and $+250°$, preferably between $-20°$ and $+80°$. At these temperatures, the esterification reactions are, as a rule, finished after 15 minutes to 48 hours.

In particular, the reaction conditions for the esterification depend substantially upon the nature of the starting materials used. Thus, a free carboxylic acid is reacted with a free alcohol or phenol, as a rule in the presence of a strong acid, for example of a mineral acid, such as hydrochloric acid or sulphuric acid. A preferred manner of reaction is the reason of an acid anhydride or especially of an acid chloride with an alcohol, preferably in a basic medium, whereby as bases especially alkali metal hydroxides, such as sodium or potassium hydroxide, alkali metal carbonates or hydrogen carbonates, such as sodium carbonate, sodium hydrogen carbonate, potassium carbonate or potassium hydrogen carbonate, alkali metal acetates, such as sodium or potassium acetate, alkaline earth metal hydroxides, such as calcium hydroxide, or organic bases, such as triethylamine, pyridine, lutidine, collidine or quinoline, are of importance. A further preferred embodimental form of the esterification consists in that one first converts the alcohol or the phenol into the sodium or potassium alcoholates or phenolates, e.g. by treatment with ethanolic sodium or potassium hydroxide solution, isolates this and, together with sodium hydrogen carbonate or potassium carbonate, suspends while stirring in acetone or diethyl ether and mixes this suspension with a solution of an acid chloride or anhydride in diethyl ether, acetone or DMF, expediently at temperatures between about $-25°$ and $+20°$.

Dioxane derivatives of the formula I (wherein one of the groups $A^1$ and/or $A^2$ signifies a 1,3-dioxane-2,5-diyl group) are expediently prepared by reaction of a corresponding aldehyde, e.g. of the formulae $R^1$-$(A^1)_{m-1}$-CHO, $R^1$-$(A^1)_m$-$Z^1$-A-$Z^2$-CHO, O=CH-$(A^1)_{m-1}$-$Z^1$-A-$Z^2$-$(A^2)_n$-$R_2$ or O=CH-$R^2$ (or of one of its reactive derivatives) with a corresponding 1,3-diol, e.g. of the formulae (HOCH$_2$)$_2$CH-$(A^1)_{m-1}$-$Z^1$-A-$Z^2$-$(A^2)_n$-$R^2$, (HOCH$_2$)$_2$CH-$R^2$, $R^1$-$(A^1)_{m-1}$-CH(CH$_2$OH)$_2$ or $R^1$-$(A^1)_m$-$Z^1$-A-$Z^2$-CH(CH$_2$OH)$_2$ (or one of its reactive derivatives), preferably in the presence of an inert solvent, such as benzene or toluene, and/or of a catalyst, e.g. of a strong acid, such as sulphuric acid, benzene- or p-toluenesulphonic acid, at temperaures between about $20°$ and about $150°$, preferably between $80°$ and $120°$. As reactive derivatives of the starting materials, there are suitable, in the first place, acetals, e.g. of the formulae $R^1$-$(A^1)_{m-1}$CH(OR$^3$)$_2$, $R^1$-$(A^1)_m$-$Z^1$-A-$Z^2$-CH(OR$^3$)$_2$, (R$^3$O)$_2$CH-$(A^1)_{m-1}$-$Z^1$-A-$Z^2$-$(A^2)_n$-$R^2$, (R$^3$O)$_2$-$R^2$, $R^4$-CH(OCH$_2$)$_2$CH-$(A^1)_{m-1}$-$Z^1$-A-$Z^2$-$(A^2)_n$-$R^2$, $R^4$-CH(OCH$_2$)$_2$CH-$R^2$, $R^1$-$(A^1)_{m-1}$-CH(CH$_2$O)$_2$-CH-$R^4$ or $R^1$-$(A^1)_m$-$Z^1$-A-$Z^2$-CH(CH$_2$O)$_2$CHR$^4$, wherein $R^3$ signifies alkyl with 1-4 C-atoms, two radicals $R^3$ together also alkylene with 2 or 3 C-atoms and $R^4$ H, alkyl with 1-4 C-atoms or phenyl.

The mentioned aldehydes and 1,3-diols, as well as their reactive derivatives, are, in part, known, in part they can be prepared without difficulties according to standard processes of organic chemistry from compounds known from the literature. For example, the aldehydes are obtainable by oxidation of corresponding alcohols or by reduction of corresponding carboxylic acids or of their derivatives, the diols by reduction of corresponding diesters.

For the preparation of nitriles of the formula I (wherein $R^1$ and/or $R^2$ signify CN), corresponding acid amides, e.g. those in which, instead of the radical $R^1$ and/or $R^2$, there stands the CONH$_2$ group, can be dehydrated. The amides are obtainable e.g. from corresponding esters or acid halides by reaction with ammonia. As agents splitting off water, there are suitable, for example, inorganic acid chlorides, such as SOCl$_2$, PCl$_3$, PCl$_5$, POCl$_3$, SO$_2$Cl$_2$, COCl$_2$, furthermore P$_2$O$_5$, P$_2$S$_5$, AlCl$_3$ (e.g. as double compound with NaCl), aromatic sulphonic acids and sulphonic acid halides. One can thereby work in the presence or absence of an inert solvent at temperatures between about $0°$ and $150°$; as solvents there come into consideration e.g. bases, such as pyridine or triethylamine, aromatic hydrocarbons, such as benzene, toluene or xylene, or amides, such as DMF.

For the preparation of the above-mentioned nitriles of formula I, one can also react corresponding acid halides, preferably the chlorides, with sulphamide, expediently in an inert solvent, such as tetramethylene sulphone, at temperatures between about $80°$ and $150°$, preferably at 120°. After usual working up, one can isolate the nitriles directly.

Ethers of the formula I (wherein $R^1$ and/or $R^2$ signify an alkyl chain, wherein one or two $CH_2$ groups are replaced by O-atoms, and/or wherein $Z^1$ and/or $Z^2$ is a -$OCH_2$- or -$CH_2O$- group) are obtainable by etherification of corresponding hydroxyl compounds, preferably of corresponding phenols, whereby the hydroxyl compound is expediently first converted into a corresponding metal derivative, e.g. by treatment with NaOH, KOH, $Na_2CO_3$ or $K_2CO_3$ into the corresponding alkali metal alcoholate or alkali metal phenolate. This can then be reacted with the corresponding alkyl halide, sulphonate or dialkyl sulphate, expediently in an inert solvent, such as acetone, DMF or dimethyl sulphoxide, or also in an excess of aqueous or aqueous alcoholic NaOH or KOH at temperatures between about 20° and 100°.

For the preparation of nitriles of the formula I (wherein $R^1$ and/or $R^2$ signify CN), the corresponding chlorine or bromine compounds of the formula I (wherein $R^1$ and/or $R^2$ signify Cl or Br) can also be reacted with a cyanide, expediently with a metal cyanide, such as NaCN, KCN or $Cu_2(CN)_2$, e.g. in the presence of pyridine, in an inert solvent, such as DMF or N-methylpyrrolidone, at temperatures between 20° and 200°.

A base of the formula I can be converted with an acid into the related acid-addition salt. For this reaction, there can be used inorganic acids, e.g. sulphuric acid, nitric acid, hydrohalic acids, such as hydrochloric acid or hydrobromic acid, phosphoric acids, such as orthophosphoric acid, sulphamic acid, furthermore organic acids, especially aliphatic, alicyclic, araliphatic, aromatic or heterocyclic mono- or polybasic carboxylic, sulphonic or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- and ethanesulphonic acid, ethanedisulphonic acid, 2-hydroxyethanesulphonic acid, benzenesulphonic acid, p-toluenesulphonic acid, naphthalene-mono- and disulphonic acid, laurylsulphuric acid.

On the other hand, it is possible to liberate the base of the formula I from an acid-addition salt of a compound of the formula I by treatment with a base, e.g. with a strong inorganic base, such as KOH or NaOH.

The dielectrics according to the invention consist of 2 to 20, preferably 3 to 12 components, among which at least one compound of the formula I. The other components are preferably chosen from the nematic or nametogenic substances, especially the known substances from the classes of the azoxybenzenes, benzylideneanilines, biphenyls, terphenyls, phenyl or cyclohexyl benzoates, cyclohexanecarboxylic acid phenyl or cyclohexyl esters, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl or cyclohexyldioxanes, possibly halogenated stilbenes, benzyl phenyl ethers, benzyl cyclohexyl ethers, cyclohexylmethyl phenyl ethers, cyclohexylmethyl cyclohexyl ethers, tolanes, substituted cinnamic acids, decalines, perhydrophenanthrenes, bicyclooctanes, 1,2-dicyclohexylethanes, 1-cyclohexyl-2-phenylethanes.

The most important compounds coming into question as components of such liquid-crystalline dielectrics can be characterised by the formula III $$R'\text{-}X\text{-}Y\text{-}Z\text{-}R'' \qquad \text{III}$$

wherein X and Z each signify a carbo- or heterocyclic ring system from the group formed by the 1,4-disubstituted benzene and cyclohexane rings 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline

| Y | —CH=CH— | —N(O)=N— |
|---|---------|----------|
|   | —CH=CQ— | —CH=N(O)— |
|   | —C≡C— | —CH$_2$—CH$_2$— |
|   | —CO—O— | —CH$_2$—O— |
|   | —CO—S— | —CH$_2$—S— |
|   | —CH=N— | —COO—Phe—COO— | or a C-C single bond, Q halogen, preferably chlorine, or -CN, and R' and R'' alkyl, alkoxy, alkanoyloxy or alkoxycarbonyloxy with up to 18, preferably up to 8 carbon atoms, or one of these residues also signifies CN, NC, $NO_2$, $CF_3$, F, Cl or Br.

In the case of most of these compounds, R' and R'' differ from one another, whereby one of these residues is usually an alkyl or alkoxy group. However, other variants of the provided substituents are also conventional. Many such substances or also mixtures thereof are commercially available.

The dielectrics according to the invention contain about 0.1 to 100, preferably 10 to 100%, of one or more compounds of the formula I.

The production of the dielectrics according to the invention takes place in the per se usual way. As a rule, the components are dissolved in one another, expediently at elevated temperature.

By suitable additives, the liquid-crystalline dielectrics according to the invention can be so modified that they can be used in all hitherto known types of liquid crystal indicator elements.

Such additives are known to the expert and are described in detail in the literature. For example, conductive salts, preferably ethyl-dimethyl-dodecylammonium 4-hexyloxybenzoate, tetrabutylammonium tetraphenyl boranate or complex salts of crown ethers (cf. e.g. I. Haller et al., Mol. Cryst. Liq. Cryst., Volume 24, pages 249–258 (1973) can be added for the improvement of the conductivity, dichroitic dyestuffs for the production of colored guest-host systems or substances for the changing of the dielectric anisotropy, of the viscosity and/or of the orientation of the nematic phases. Such substances are described, e.g., in published Federal Republic of Germany Patent Specifications Nos. 22 09 127, 22 40 864, 23 21 632, 23 38 281, 24 50 088, 26 37 430, 28 53 728 and 29 02 177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and C is the clear point of a liquid crystal substance.

"Usual working up" means: one adds water thereto, extracts with methylene chloride, separates off, dries the organic phase, evaporates and purifies the product by crystallization and/or chromotography.

EXAMPLE 1

One cools 10 g. acetophenone to 2° and mixes, while stirring, below 20° with 10.4 g. $SnCl_4$. With stirring, one adds dropwise thereto at 20°, within 1 hour, 13.4 g. p-methylstyrene oxide, warms the mixture to 28°, works up as usual with diethyl ether/10% aqueous sodium hydroxide solution and obtains trans-2,5-di-p-tolyl-1,4-dioxane, m.p. 200°, C 110°, Rf 0.45 (silica gel/toluene).

from the corresponding stryene oxides, one obtains analogously:
trans-2-p-tolyl-5-p-ethylphenyl-1,4-dioxane
trans-2-p-tolyl-5-p-propylphenyl-1,4-dioxane
trans-2-p-tolyl-5-p-isopropylphenyl-1,4-dioxane
trans-2-p-tolyl-5-p-butylphenyl-1,4-dioxane
trans-2-p-tolyl-5-p-pentylphenyl-1,4-dioxane
trans-2-p-tolyl-5-p-hexylphenyl-1,4-dioxane
trans-2,5-bis-p-ethylphenyl-1,4-dioxane
trans-2-p-ethylphenyl-5-p-propylphenyl-1,4-dioxane
trans-2-p-ethylphenyl-5-p-isopropylphenyl-1,4-dioxane
trans-2-p-ethylphenyl-5-p-butylphenyl-1,4-dioxane
trans-2-p-ethylphenyl-5-p-pentylphenyl-1,4-dioxane
trans-2-p-ethylphenyl-5-p-hexylphenyl-1,4-dioxane
trans-2,5-bis-p-propylphenyl-1,4-dioxane
trans-2-p-propylphenyl-5-p-isopropylphenyl-1,4-dioxane
trans-2-p-propylphenyl-5-p-butylphenyl-1,4-dioxane
trans-2-p-propylphenyl-5-p-pentylphenyl-1,4-dioxane
trans-2-p-propylphenyl-5-p-hexylphenyl-1,4-dioxane
trans-2,5'-bis-p-isopropylphenyl-1,4-dioxane
trans-2-p-isopropylphenyl-5-p-butylphenyl-1,4-dioxane
trans-2-p-isopropylphenyl-5-p-pentylphenyl-1,4-dioxane
trans-2-p-isopropylphenyl-5-p-hexylphenyl-1,4-dioxane
trans-2,5-bis-p-butylphenyl-1,4-dioxane
trans-2-p-butylphenyl-5-p-pentylphenyl-1,4-dioxane
trans-2-p-butylphenyl-5-p-hexylphenyl-1,4-dioxane
trans-2,5-bis-p-isobutylphenyl-1,4-dioxane
trans-2,5-bis-p-pentylphenyl-1,4-dioxane
trans-2-p-pentylphenyl-5-p-hexylphenyl-1,4-dioxane
trans-2,5-bis-p-hexylphenyl-1,4-dioxane.

EXAMPLE 2

One boils a solution of 29.6 g. 1-p-ethoxyphenyl-4-hydroxymethyl-3-oxa-nonan-1-ol (obtainable by reaction of p-ethoxyphenacyl bromide with 2-hydroxyheptanoic acid ethyl ester to give 2-p-ethoxyphenacyloxyheptanoic acid ethyl ester and reduction with $LiAlH_4$) and 1 g. p-toluenesulphonic acid in 400 ml. toluene for 1 hour with water separator, washes with $NaHCO_3$ solution, dries, evaporates and obtains trans-2-p-ethoxyphenyl-5-pentyl-1,4-dioxane.

From the corresponding diols, one obtains analogously:
trans-2-phenyl-5-pentyl-1,4-dioxane
trans-2-p-ethylphenyl-5-ethyl-1,4-dioxane
trans-2-p-ethylphenyl-5-propyl-1,4-dioxane
trans-2-p-ethylphenyl-5-butyl-1,4-dioxane
trans-2-p-ethylphenyl-5-pentyl-1,4-dioxane
trans-2-p-ethylphenyl-5-hexyl-1,4-dioxane
trans-2-p-ethylphenyl-5-heptyl-1,4-dioxane
trans-2-p-propylphenyl-5-ethyl-1,4-dioxane
trans-2-p-propylphenyl-5-propyl-1,4-dioxane
trans-2-p-propylphenyl-5-butyl-1,4-dioxane
trans-2-p-propylphenyl-5-pentyl-1,4-dioxane
trans-2-p-propylphenyl-5-hexyl-1,4-dioxane
trans-2-p-propylphenyl-5-heptyl-1,4-dioxane
trans-2-p-butylphenyl-5-ethyl-1,4-dioxane
trans-2-p-butylphenyl-5-propyl-1,4-dioxane
trans-2-p-butylphenyl-5-butyl-1,4-dioxane
trans-2-p-butylphenyl-5-pentyl-1,4-dioxane
trans-2-p-butylphenyl-5-hexyl-1,4-dioxane
trans-2-p-butylphenyl-5-heptyl-1,4-dioxane
trans-2-p-pentylphenyl-5-ethyl-1,4-dioxane
trans-2-p-pentylphenyl-5-propyl-1,4-dioxane
trans-2-p-pentylphenyl-5-butyl-1,4-dioxane
trans-2-p-pentylphenyl-5-pentyl-1,4-dioxane
trans-2-p-pentylphenyl-5-hexyl-1,4-dioxane
trans-2-p-pentylphenyl-5-heptyl-1,4-dioxane
trans-2-p-hexylphenyl-5-ethyl-1,4-dioxane
trans-2-p-hexylphenyl-5-propyl-1,4-dioxane
trans-2-p-hexylphenyl-5-butyl-1,4-dioxane
trans-2-p-hexylphenyl-5-pentyl-1,4-dioxane
trans-2-p-hexylphenyl-5-hexyl-1,4-dioxane
trans-2-p-hexylphenyl-5-heptyl-1,4-dioxane
trans-2-p-hexylphenyl-5-ethyl-1,4-dioxane
trans-2-p-heptylphenyl-5-propyl-1,4-dioxane
trans-2-p-heptylphenyl-5-butyl-1,4-dioxane
trans-2-p-heptylphenyl-5-pentyl-1,4-dioxane
trans-2-p-heptylphenyl-5-hexyl-1,4-dioxane
trans-2-p-heptylphenyl-5-heptyl-1,4-dioxane
trans-2-p-methoxyphenyl-5-ethyl-1,4-dioxane
trans-2-p-methoxyphenyl-5-propyl-1,4-dioxane
trans-2-p-methoxyphenyl-5-butyl-1,4-dioxane
trans-2-p-methoxyphenyl-5-pentyl-1,4-dioxane
trans-2-p-methoxyphenyl-5-hexyl-1,4-dioxane
trans-2-p-methoxyphenyl-5-heptyl-1,4-dioxane
trans-2-p-ethoxyphenyl-5-ethyl-1,4-dioxane
trans-2-p-ethoxyphenyl-5-propyl-1,4-dioxane
trans-2p-ethoxyphenyl-5-butyl-1,4-dioxane
trans-2-p-ethoxyphenyl-5-hexyl-1,4-dioxane
trans-2-p-ethoxyphenyl-5-heptyl-1,4-dioxane
trans-2-p-propoxyphenyl-5-ethyl-1,4-dioxane
trans-2-p-propoxyphenyl-5-propyl-1,4-dioxane
trans-2-p-propoxyphenyl-5-butyl-1,4-dioxane
trans-2-p-propoxyphenyl-5-pentyl-1,4-dioxane
trans-2-p-propoxyphenyl-5-hexyl-1,4-dioxane
trans-2-propoxyphenyl-5-heptyl-1,4-dioxane
trans-2-p-butoxyphenyl-5-ethyl-1,4-dioxane trans-2-p-butoxyphenyl-5-propyl-1,4-dioxane
trans-2-p-butoxyphenyl-5-butyl-1,4-dioxane
trans-2-p-butoxyphenyl-5-pentyl-1,4-dioxane
trans-2-p-butoxyphenyl-5-hexyl-1,4-dioxane
trans-2-p-butoxyphenyl-5-heptyl-1,4-dioxane
trans-2-p-pentoxyphenyl-5-ethyl-1,4-dioxane
trans-2-p-pentoxyphenyl-5-propyl-1,4-dioxane
trans-2-p-pentoxyphenyl-5-butyl-1,4-dioxane
trans-2-p-pentoxyphenyl-5-pentyl-1,4-dioxane
trans-2-p-pentoxyphenyl-5-hexyl-1,4-dioxane
trans-2-p-pentoxyphenyl-5-heptyl-1,4-dioxane
trans-2-p-hexoxyphenyl-5-ethyl-1,4-dioxane
trans-2-p-hexoxyphenyl-5-propyl-1,4-dioxane
trans-2-p-hexoxyphenyl-5-butyl-1,4-dioxane
trans-2-p-hexoxyphenyl-5-pentyl-1,4-dioxane
trans-2-p-hexoxyphenyl-5-hexyl-1,4-dioxane
trans-2-p-hexoxyphenyl-5-heptyl-1,4-dioxane
trans-2-p-(trans-4-ethylcyclohexyl)-phenyl-5-ethyl-1,4-dioxane
trans-2-p-(trans-2-ethylcyclohexyl)-phenyl-5-propyl-1,4-dioxane
trans-2-p-(trans-2-ethylcyclohexyl)-phenyl-5-butyl-1,4-dioxane
trans-2-p-(trans-2-ethylcyclohexyl)-phenyl-5-pentyl-1,4-dioxane
trans-2-p-(trans-2-ethylcyclohexyl)-phenyl-5-hexyl-1,4-dioxane
trans-2-p-(trans-2-ethylcyclohexyl)-phenyl-5-heptyl-1,4-dioxane
trans-2-p-(trans-4-propylcyclohexyl)-phenyl-5-ethyl-1,4-dioxane
trans-2-p-(trans-2-propylcyclohexyl)-phenyl-5-propyl-1,4-dioxane
trans-2-p-(trans-2-propylcyclohexyl)-phenyl-5-butyl-1,4-dioxane
trans-2-p-(trans-2-propylcyclohexyl)-phenyl-5-pentyl-1,4-dioxane
trans-2-p-(trans-2-propylcyclohexyl)-phenyl-5-hexyl-1,4-dioxane
trans-2-p-(trans-2-propylcyclohexyl)-phenyl-5-heptyl-1,4-dioxane
trans-2-p-(trans-4-butylcyclohexyl)-phenyl-5-ethyl-1,4-dioxane
trans-2-p-(trans-4-butylcyclohexyl)-phenyl-5-propyl-1,4-dioxane
trans-2-p-(trans-4-butylcyclohexyl)-phenyl-5-butyl-1,4-dioxane
trans-2-p-(trans-4-butylcyclohexyl)-phenyl-5-pentyl-1,4-dioxane
trans-2-p-(trans-4-butylcyclohexyl)-phenyl-5-hexyl-1,4-dioxane
trans-2-p-(trans-4-butylcyclohexyl)-phenyl-5-heptyl-1,4-dioxane
trans-2-p-(trans-4-pentylcyclohexyl)-phenyl-5-ethyl-1,4-dioxane
trans-2-p-(trans-4-pentylcyclohexyl)-phenyl-5-propyl-1,4-dioxane
trans-2-p-(trans-4-pentylcyclohexyl)-phenyl-5-butyl-1,4-dioxane
trans-2-p-(trans-4-pentylcyclohexyl)-phenyl-5-pentyl-1,4-dioxane
trans-2-p-(trans-4-pentylcyclohexyl)-phenyl-5-hexyl-1,4-dioxane
trans-2-p-(trans-4-pentylcyclohexyl)-phenyl-5-heptyl-1,4-dioxane
trans-2-p-(trans-4-hexylcyclohexyl)-phenyl-5-ethyl-1,4-dioxane
trans-2-p-(trans-4-hexylcyclohexyl)-phenyl-5-propyl-1,4-dioxane
trans-2-p-(trans-4-hexylcyclohexyl)-phenyl-5-butyl-1,4-dioxane
trans-2-p-(trans-4-hexylcyclohexyl)-phenyl-5-pentyl-1,4-dioxane
trans-2-p-(trans-4-hexylcyclohexyl)-phenyl-5-hexyl-1,4-dioxane
trans-2-p-(trans-4-hexylcyclohexyl)-phenyl-5-heptyl-1,4-dioxane
trans-2-p-(trans-4-heptylcyclohexyl)-phenyl-5-ethyl-1,4-dioxane
trans-2-p-(trans-4-heptylcyclohexyl)-phenyl-5-propyl-1,4-dioxane
trans-2-p-(trans-4-heptylcyclohexyl)-phenyl-5-butyl-1,4-dioxane
trans-2-p-(trans-4-heptylcyclohexyl)-phenyl-5-pentyl-1,4-dioxane
trans-2-p-(trans-4-heptylcyclohexyl)-phenyl-5-hexyl-1,4-dioxane
trans-2-p-(trans-4-heptylcyclohexyl)-phenyl-5-heptyl-1,4-dioxane
trans-2-(2-p-methoxyphenylethyl)-5-pentyl-1,4-dioxane
trans-2-m-fluorophenyl-5-pentyl-1,4-dioxane
trans-2-p-fluorophenyl-5-pentyl-1,4-dioxane
trans-2-p-chlorophenyl-5-pentyl-1,4-dioxane
trans-2-p-bromophenyl-5-pentyl-1,4-dioxane
trans-2-p-methoxymethylphenyl-5-pentyl-1,4-dioxane
trans-2-p-methoxymethoxyphenyl-5-pentyl-1,4-dioxane
trans-2-p-methoxyphenyl-1,4-dioxane.

EXAMPLE 3

A solution of 4.06 g. 4-hydroxymethyl-3-oxa-1-phenyl-nonan-1-ol 1-mono-p-toluene sulphonate (obtainable by reaction of styrene oxide with heptane-1,2-diol and partial tosylation of the 4-hydroxymethyl-3-oxa-1-phenylnonan-1-ols obtained) in 100 ml. phosphoric acid hexamethyltriamide is heated for 24 hours to 80°. One evaporates, works up as usual and obtains 2-phenyl-5-pentyl-1,4-dioxane as an oily isomer mixture. Isomerization of 1 g. of the mixture by 2 hours heating with 0.05 g. K tert.-butylate in 10 ml. dimethyl sulphoxide to 80° leads to trans-2-phenyl-5-pentyl-1,4-dioxane.

One obtains analogously:
trans-2-(4'-methyl-4-biphenylyl)-5-ethyl-1,4-dioxane
trans-2-(4'-methyl-4-biphenylyl)-5-propyl-1,4-dioxane
trans-2-(4'-methyl-4-biphenylyl)-5-butyl-1,4-dioxane
trans-2-(4'-methyl-4-biphenylyl)-5-pentyl-1,4-dioxane
trans-2-(4'-methyl-4-biphenylyl)-5-hexyl-1,4-dioxane
trans-2-(4'-methyl-4-biphenylyl)-5-heptyl-1,4-dioxane
trans-2-(4'-ethyl-4-biphenylyl)-5-ethyl-1,4-dioxane
trans-2-(4'-ethyl-4-biphenylyl)-5-propyl-1,4-dioxane
trans-2-(4'-ethyl-4-biphenylyl)-5-butyl-1,4-dioxane
trans-2-(4'-ethyl-4-biphenylyl)-5-pentyl-1,4-dioxane
trans-2-(4'-ethyl-4-biphenylyl)-5-hexyl-1,4-dioxane
trans-2-(4'-ethyl-4-biphenylyl)-5-heptyl-1,4-dioxane
trans-2-(4'-propyl-4-biphenylyl)-5-ethyl-1,4-dioxane
trans-2-(4'-propyl-4-biphenylyl)-5-propyl-1,4-dioxane
trans-2-(4'-propyl-4-biphenylyl)-5-butyl-1,4-dioxane
trans-2-(4'-propyl-4-biphenylyl)-5-pentyl-1,4-dioxane
trans-2-(4'-propyl-4-biphenylyl)-5-hexyl-1,4-dioxane
trans-2-(4'-propyl-4-biphenylyl)-5-heptyl-1,4-dioxane
trans-2-(4'-butyl-4-biphenylyl)-5-ethyl-1,4-dioxane
trans-2-(4'-butyl-4-biphenylyl)-5-propyl-1,4-dioxane
trans-2-(4'butyl-4-biphenylyl)-5-butyl-1,4-dioxane
trans-2-(4'-butyl-4-biphenylyl)-5-pentyl-1,4-dioxane
trans-2-(4'-butyl-4-biphenylyl)-5-hexyl-1,4-dioxane
trans-2-(4'-butyl-4-biphenylyl)-5-heptyl-1,4-dioxane trans-2-(4'-pentyl-4-biphenylyl)-5-ethyl-1,4-dioxane
trans-2-(4'-pentyl-4-biphenylyl)-5-propyl-1,4-dioxane
trans-2-(4'-pentyl-4-biphenylyl)-5-butyl-1,4-dioxane
trans-2-(4'-pentyl-4-biphenylyl)-5-pentyl-1,4-dioxane
trans-2-(4'-pentyl-4-biphenylyl)-5-hexyl-1,4-dioxane
trans-2-(4'-pentyl-4-biphenylyl)-5-heptyl-1,4-dioxane
trans-2-(4'-hexyl-4-biphenylyl)-5-ethyl-1,4-dioxane
trans-2-(4'-hexyl-4-biphenylyl)-5-propyl-1,4-dioxane
trans-2-(4'-hexyl-4-biphenylyl)-5-butyl-1,4-dioxane
trans-2-(4'-hexyl-4-biphenylyl)-5-pentyl-1,4-dioxane
trans-2-(4'-hexyl-4-biphenylyl)-5-hexyl-1,4-dioxane
trans-2-(4'-hexyl-4-biphenylyl)-5-heptyl-1,4-dioxane
trans-2-(4'-heptyl-4-biphenylyl)-5-ethyl-1,4-dioxane
trans-2-(4'-heptyl-4-biphenylyl)-5-propyl-1,4-dioxane
trans-2-(4'-heptyl-4-biphenylyl)-5-butyl-1,4-dioxane
trans-2-(4'-heptyl-4-biphenylyl)-5-pentyl-1,4-dioxane
trans-2-(4'-heptyl-4-biphenylyl)-5-hexyl-1,4-dioxane
trans-2-(4'-heptyl-4-biphenylyl)-5-heptyl-1,4-dioxane
trans-2-(4'-(trans-4-ethylcyclohexyl)-4-biphenylyl)-5-ethyl-1,4-dioxane
trans-2-(4'-(trans-4-ethylcyclohexyl)-4-biphenylyl)-5-propyl-1,4-dioxane
trans-2-(4'-(trans-4-ethylcyclohexyl)-4-biphenylyl)-5-butyl-1,4-dioxane
trans-2-(4'-(trans-4-ethylcyclohexyl)-4-biphenylyl)-5-pentyl-1,4-dioxane
trans-2-(4'-(trans-4-ethylcyclohexyl)-4-biphenylyl)-5-hexyl-1,4-dioxane
trans-2-(4'-(trans-4-ethylcyclohexyl)-4-biphenylyl)-5-heptyl-1,4-dioxane
trans-2-(4'-(trans-4-propylcyclohexyl)-4-biphenylyl)-5-ethyl-1,4-dioxane
trans-2-(4'-(trans-4-propylcyclohexyl)-4-biphenyl)-5-propyl-1,4-dioxane
trans-2-(4'-(trans-4-propylcyclohexyl)-4-biphenylyl)-5-butyl-1,4-dioxane
trans-2-(4'-(trans-4-propylcyclohexyl)-4-biphenylyl)-5-pentyl-1,4-dioxane
trans-2-(4'-(trans-4-propylcyclohexyl)-4-biphenylyl)-5-hexyl-1,4-dioxane
trans-2-(4'-(trans-4-propylcyclohexyl)-4-biphenylyl)-5-heptyl-1,4-dioxane
trans-2-(4'-(butylcyclohexyl)-4-biphenylyl)-5-ethyl-1,4-dioxane
trans-2-(4'-(trans-4-butylcyclohexyl)-4-biphenylyl)-5-propyl-1,4-dioxane
trans-2-(4'-(trans-4-butylcyclohexyl)-4-biphenylyl)-5-butyl-1,4-dioxane
trans-2-(4'-(trans-4-butylcyclohexyl)-4-biphenylyl)-5-pentyl-1,4-dioxane
trans-2-(4'-(trans-4-butylcyclohexyl)-4-biphenylyl)-5-hexyl-1,4-dioxane
trans-2-(4'-(trans-4-butylcyclohexyl)-4-biphenylyl)-5-heptyl-1,4-dioxane
trans-2-(4'-(trans-4-pentylcyclohexyl)-4-biphenylyl)-5-ethyl-1,4-dioxane
trans-2-(4'-(trans-4-pentylcyclohexyl)-4-biphenylyl)-5-propyl-1,4-dioxane
trans-2-(4'-(trans-4-pentylcyclohexyl)-4-biphenylyl)-5-butyl-1,4-dioxane
trans-2-(4'-(trans-4-pentylcyclohexyl)-4-biphenylyl)-5-pentyl-1,4-dioxane
trans-2-(4'-(trans-4-pentylcyclohexyl)-4-biphenylyl)-5-hexyl-1,4-dioxane
trans-2-(4-(trans-4-pentylcyclohexyl)-4-biphenylyl)-5-heptyl-1,4-dioxane
trans-2-(4'-(trans-4-hexylcyclohexyl)-4-biphenylyl)-5-ethyl-1,4-dioxane
trans-2-(4'-(trans-4-hexylcyclohexyl)-4-biphenylyl)-5-propyl-1,4-dioxane
trans-2-(4'-(trans-4-hexylcyclohexyl)-4-biphenylyl)-5-butyl-1,4-dioxane
trans-2-(4'-(trans-4-hexylcyclohexyl)-4-biphenylyl)-5-pentyl-1,4-dioxane
trans-2-(4'-(trans-4-hexylcyclohexyl)-4-biphenylyl)-5-hexyl-1,4-dioxane
trans-2-(4'-(trans-4-hexylcyclohexyl)-4-biphenylyl)-5-heptyl-1,4-dioxane.

EXAMPLE 4

A mixture of 2.96 g. 3-fluoro-4-(trans-5-pentyl-1,4-dioxane-2-yl)benzoic acid (obtainable from the nitrile, cf. Example 7), 1.42 g. trans-4-propylcyclohexanol and 2.06 g. dicyclohexylcarbodiimide is boiled in 50 ml. diethyl ether for 6 hours. After cooling, one filters, works up as usual and obtains 3-fluoro-4-(trans-5-pentyl-1,4-dioxan-2-yl)benzoic acid trans-4-propylcyclohexyl ester.

One obtains analogously by esterification:
trans-2-pethoxyphenyl-1,4-dioxane-5-carboxylic acid p-ethoxyphenyl ester
p-(trans-5-pentyl-1,4-dioxan-2-yl)-benzoic acid trans-4-methoxymethylcyclohexyl ester
p-(trans-5-pentyl-1,4-dioxan-2-yl)-benzoic acid p-2-methoxyethoxyphenyl ester
p-(trans-5-pentyl-1,4-dioxan-2-yl)-benzoic acid 2,3,5,6-tetrafluorophenyl ester
p-(trans-5-pentyl-1,4-dioxan-2-yl)-benzoic acid 1-propyl-4-piperidyl ester
p-(trans-5-pentyl-1,4-dioxan-2-yl)-benzoic acid 1,4-bicyclo(2,2,2)octyl ester
p-(trans-5-pentyl-1,4-dioxan-2-yl)-benzoic acid 5-methoxypyrimidin-2-yl ester.

EXAMPLE 5

One boils 27.8 g. (trans-5-pentyl-1,4-dioxanyl)-benzoic acid (obtainable by reaction of trans-2-phenyl-5-pentyl-1,4-dioxane with CH₃COCl/AlCl₃ to give 2-p-acetylphenyl-5-pentyl-1,4-dioxane and decomposition with bromine/KOH) for 1 hour with 24 g. SOCl₂, dissolves the crude acid chloride obtained in 150 ml. toluene, mixes with 8 ml. pyridine and 16.6 g. trans-4-pentylcyclohexanol and boils for 2 hours. After cooling and usual working up, one obtains p-(trans-5-pentyl-1,4-dioxan-2-yl)-benzoic acid trans-4-pentylcyclohexyl ester.

EXAMPLE 6

A mixture of 1.2 g. 2-propylpropan-1,3-diol, 2.2 g. trans-5-formyl-2-p-methoxyphenyl-1,4-dioxane (obtainable by reaction of 1,1-ethylenedioxypropan-2,3-diol with p-methoxystyrene oxide and hydrolysis), 0.01 g. p-toluene sulphonic acid and 15 ml. toluene is boiled on a water separator for 3 hours, cooled, washed with water and evaporated. One obtains trans-2-p-methoxyphenyl-5-(trans-5-propyl-1,3-dioxan-2-yl)-1,4-dioxane.

EXAMPLE 7

A solution of 29.5 g. trans-2-fluoro-4-(5-pentyl-1,4-dioxan-2-yl)-benzamide (obtainable from the acid chloride and NH₃) in 500 ml. DMF is mixed dropwise at 50°, while stirring, with 65 g. POCl₃. After a further one hour stirring, one pours on to ice, works up as usual and obtains trans-2-fluoro-4-(5-pentyl-1,4-dioxan-2-yl)-benzonitrile.

From the corresponding amides, one obtains analogously:
trans-2-p-cyanophenyl-5-methyl-1,4-dioxane
trans-2-p-cyanophenyl-5-ethyl-1,4-dioxane
trans-2-p-cyanophenyl-5-propyl-1,4-dioxane
trans-2-p-cyanophenyl-5-butyl-1,4-dioxane
trans-2-p-cyanophenyl-5-pentyl-1,4-dioxane
trans-2-p-cyanophenyl-5-hexyl-1,4-dioxane
trans-2-p-cyanophenyl-5-heptyl-1,4-dioxane
trans-2-p-cyanophenyl-5-octyl-1,4-dioxane
trans-2-p-cyanophenyl-5-nonyl-1,4-dioxane
trans-2-p-cyanophenyl-5-decyl-1,4-dioxane
trans-2-(4'-cyano-4-biphenylyl)-5-ethyl-1,4-dioxane
trans-2-(4'-cyano-4-biphenylyl)-5-propyl-1,4-dioxane
trans-2-(4'-cyano-4-biphenylyl)-5-butyl-1,4-dioxane
trans-2-(4'-cyano-4-biphenylyl)-5-pentyl-1,4-dioxane
trans-2-(4'-cyano-4-biphenylyl)-5-hexyl-1,4-dioxane
trans-2-(4'-cyano-4-biphenylyl)-5-heptyl-1,4-dioxane
trans-2-(2-fluoro-4-cyanophenyl)-5-pentyl-1,4-dioxane.

EXAMPLE 8

A solution of 29.7 g. p-(trans-5-pentyl-1,4-dioxan-2-yl)-benzoyl chloride and 8 g. sulphamide in 500 ml. tetramethylene sulphone is heated for 4 hours at 120°, evaporated and worked up as usual. One obtains trans-2-p-cyanophenyl-5-pentyltetrahydropyran. The other nitriles mentioned in Example 7 are obtained analogously.

EXAMPLE 9

A mixture of 25 g. trans-2-p-hydroxyphenyl-5-pentyl-1,4-dioxane (obtainable by nitration of trans-2-phenyl-5-pentyl-1,4-dioxane, hydrogenation of the trans-2-p-nitrophenyl-5-pentyl-1,4-dioxane obtained to give trans-2-p-aminophenyl-5-pentyl-1,4-dioxane, diazotisation and hydrolysis), 6.9 g. $K_2CO_3$, 25 g. $K_2CO_3$, 25 g. hexyl iodide and 250 ml. DMF is heated, while stirring, for 16 hours at 80°, then cooled and up as usual. One obtains trans-2-p-hexoxyphenyl-5-pentyl-1,4-dioxane.

From p-ethoxyphenol and trans-2-bromomethyl-5-pentyl-1,4-dioxane, one obtains analogously trans-2-p-ethoxyphenoxymethyl-5-pentyl-1,4-dioxane.

EXAMPLE 10

A mixture of 31.3 g. trans-2-p-bromophenyl-5-pentyl-1,4-dioxane, 10 g. $Cu_2(CN)_2$, 120 ml. pyridine and 60 ml. N-methylpyrrolidone is heated for 2 hours to 150°. One cools, adds thereto a solution of 120 g. $FeCl_3.6H_2O$ in 600 ml. 20% hydrochloric acid, heats to 70° for 1.5 hours, while stirring. Works up as usu 1 and obtains trans-2-p-cyanophenyl-5-pentyl-1,4-dioxane.

The other nitriles mentioned in Example 7 are obtainable analogously.

There follow Examples of dielectrics according to the invention with a content of at least one compound of the formula I:

EXAMPLE A

One prepares a mixture of
22% trans-2,5-bis-(p-isopropylphenyl)-1,4-dioxane
17% p-trans-4-propylcyclohexylbenzonitrile
23% p-trans-4-pentylcyclohexylbenzonitrile
16% trans-1-p-ethoxyphenyl-4-propylcyclohexane
12% trans-1-p-butoxyphenyl-4-propylcyclohexan and
10% 4-(trans-4-pentylcyclohexyl)-4'-(trans-4-propylcyclohexyl)-biphenyl.

EXAMPLE B

One prepares a mixture of:
20% trans-2-p-cyanophenyl-5-propyl-1,4-dioxane
13% trans-1p-ethylphenyl-4-propylcyclohexane
31% trans-1-p-ethoxyphenyl-4-propylcyclohexane
31% 4-ethyl-4'-(trans-4-propylcyclohexyl)-biphenyl and
5% 4-(trans-4-pentylcyclohexyl)-4'-(trans-4-propylcyclohexyl)-biphenyl.

EXAMPLE C

One prepares a mixture of:
16% trans-2-p-ethylphenyl-5-propyl-1,4-dioxane
15% p-trans-4-propylcyclohexylbenzonitrile
11% p-trans-4-butylcyclohexylbenzonitrile
21% p-trans-4-pentylcyclohexylbenzonitrile
21% 4-ethyl-4'-(trans-4-pentylcyclohexyl)-biphenyl
11% 4-(trans-4-pentylcyclohexyl)-4'-(trans-4-propylcyclohexyl)-biphenyl and
5% 4-cyano-4'-(trans-4-pentylcyclohexyl)-biphenyl.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline dielectric useful in an electro-optical indicator element and comprising at least two liquid-crystalline compounds, wherein at least one such component is a compound of the formula

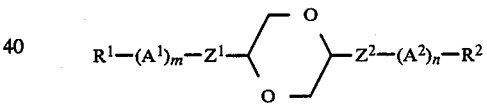

wherein
R$^1$ and R$^2$ each independently is alkyl of 1–10 C-atoms, F, Cl, Br, CN or alkyl of 1–10 C-atoms wherein one or two non-adjacent CH$_2$ groups are replaced by O atoms,
R$^2$ can also be H,
A$^1$ and A$^2$ each is 1,4-phenylene, 1,4-cyclohexylene, 1,3-dioxane-2,5-diyl, 1,4-dioxane-2,5-diyl, piperidine-1,4-diyl, 1,4-bicyclo(2,2,2)-octylene or pyrimidine-2,5-diyl, unsubstituted or substituted by 1–4 F-atoms,
Z$^1$ and Z$^2$ each independently is -CO-O-, -O-CO-, -CH$_2$CH$_2$-, -OCH$_2$-, -CH$_2$O- or a single bond,
m and n each independently is 0, 1, 2 or 3,
when m is zero, Z$^1$ is a direct bond, when n is zero, Z$^2$ is a direct bond
(m+n) is at least 1 and at most 3, whereby for m=2 or 3, the groups A$^1$, and for n=2 or 3, the groups A$^2$ can, in each case, be the same or different from one another, with the proviso that Z$^1$ and Z$^2$ are not both ester groups.

2. A liquid-crystalline dielectric of claim 1 wherein the compound is of the formula R$^1$-A$^1$-Z$^1$-A-Z$^2$-R$^2$, or R$^1$-Z$^1$-A-Z$^2$-A$^2$-R$^2$, wherein "A" is 1,4-dioxane-2,5-diyl.

3. A liquid-crystalline dielectric of claim 1 wherein the compound is of the formula $R^1-(A^1)_2-Z^1-A-Z^2-R^2$, $R^1-A^1-Z^1-A-Z^2-A^2-R^2$ or $R^1-Z^1-A-Z^2-(A^2)_2-R^2$, wherein "A" is 1,4-dioxane-2,5-diyl.

4. A liquid-crystalline dielectric of claim 1 wherein the compound is of the formula
$R^1-(A^1)_3-Z^1-A-Z^2-R^2$,
$R^1-(A^1)_2-Z^1-A-Z^2-A^2-R^2$,
$R^1-A^1-Z^1-A-Z^2-(A^2)_2-R^2$, or
$R^1-Z^1-A-Z^2-(A^2)_3-R^2$,
wherein "A" is 1,4-dioxane-2,5-diyl.

5. A liquid-crystalline dielectric of claim 2 wherein the compound is of the formula
$R^1-Phe-Z^1-A-Z^2-R^2$,
$R^1-Cy-Z^1-A-Z^2-R^2$,
$R^1-Dio-Z^1-A-Z^2-R^2$,
$R^1-Pip-Z^1-A-Z^2-R^2$,
$R^1-Bi-Z^1-A-Z^2-R^2$, or
$R^1-Pyr-Z^1-A-Z^2-R^2$,
wherein "Phe" is 1,4-phenylene, "Cy" is 1,4-cyclohexylene, "Dio" is 1,3-dioxane-2,5-diyl, "Bi" is bicyclo(2,2,2)-octylene, "Pip" is piperidine-1,4-diyl and "Pyr" is pyrimidine-2,5-diyl.

6. A liquid-crystalline dielectric of claim 2 wherein the compound is of the formula
$R^1-Z^1-A-Z^2-Phe-R^2$,
$R^1-Z^1-A-Z^2-Cy-R^2$,
$R^1-Z^1-A-Z^2-Dio-R^2$,
$R^1-Z^1-A-Z^2-Pip-R^2$,
$R^1-Z^1-A-Z^2-Bi-R^2$, or
$R^1-Z^1-A-Z^2-Pyr-R^2$,
wherein "Phe" is 1,4-phenylene, "Cy" is 1,4-cyclohexylene, "Dio" is 1,3-dioxane-2,5-diyl, "Bi" is bicyclo(2,2,2)-octylene, "Pip" is piperidine-1,4-diyl and "Pyr" is pyrimidine-2,5-diyl.

7. A liquid-crystalline dielectric of claim 6 wherein the compound is of the formula $R^1-Z^1-A-Z^2-Phe-R^2$.

8. A liquid-crystalline dielectric of claim 1 wherein the compound is of the formula $R^1-Z^1-A-Z^2-(A^2)_2-R^2$ or $R^1-Z^1-A-Z^2-(A^2)_3-R^2$, wherein "A" is 1,4-dioxane-2,5-diyl.

9. A liquid-crystalline dielectric of claim 1 wherein the compound is of the formula
$R^1-Phe-Phe-Z^1-A-Z^2-R^2$,
$R^1-Phe-Cy-Z^1-A-Z^2-R^2$,
$R^1-Cy-Phe-Z^1-A-Z^2-R^2$,
$R^1-Cy-Cy-Z^1-A-Z^2-R^2$,
$R^1-Phe-Z^1-A-Z^2-Phe-R^2$,
$R^1-Phe-Z^1-A-Z^2-Cy-R^2$,
$R^1-Cy-Z^1-A-Z^2-Phe-R^2$,
$R^1-Cy-Z^1-A-Z-Cy-R^2$,
$R^1-Z^1-A-Z^2-Phe-Phe-R^2$,
$R^1-Z^1-A-Z^2-Phe-Cy-R^2$,
$R^1-Z^1-A-Z^2-Cy-Phe-R^2$,
$R^1-Z^1A-Z^2-Cy-Cy-R^2$,
$R^1-Phe-Phe-Phe-Z^1-A-Z^2-R^2$,
$R^1-Phe-Phe-Cy-Z^1-A-Z^2-R^2$,
$R^1-Phe-Cy-Phe-Z^1-A-Z^2-R^2$,
$R^1-Phe-Cy-Cy-Z^1-A-Z^2-R^2$,
$R^1-Cy-Phe-Phe-Z^1-A-Z^2-R^2$,
$R^1-Cy-Phe-Cy-Z^1-A-Z^2-R^2$,
$R^1-Cy-Cy-Phe-Z^1-A-Z^2-R^2$,
$R^1-Cy-Cy-Cy-Z^1-A-Z^2-R^2$,
$R^1-Phe-Phe-Z^1-A-Z^2-Phe-R^2$,
$R^1-Phe-Phe-Z^1-A-Z^2-Cy-R^2$,
$R^1-Phe-Cy-Z^1-A-Z^2-Phe-R^2$,
$R^1Phe-Cy-Z^1-A-Z^2-Cy-R^2$,
$R^1-Cy-Phe-Z^1-A-Z^2-Phe-R^2$,
$R^1-Cy-Phe-Z^1-A-Z^2-Cy-R^2$,
$R^1-Cy-Cy-Z^1-A-Z^2-Phe-R^2$,
$R^1-Cy-Cy-Z^1-A-Z^2-Cy-R^2$,
$R^1-Phe-Z^1-A-Z^2-Phe-Phe-R^2$,
$R^1-Phe-Z^1-A-Z^2-Phe-Cy-R^2$,
$R^1-Phe-Z^1-A-Z^2-Cy-Phe-R^2$,
$R^1-Phe-Z^1-A-Z^2-Cy-Cy-R^2$,
$R^1-Cy-Z^1-A-Z^2-Phe-Phe-R^2$,
$R^1-Cy-Z^1-A-Z^2-Phe-Cy-R^2$,
$R^1-Cy-Z^1-A-Z^2-Cy-Phe-R^2$,
$R^1-Cy-Z^1-A-Z^2-Cy-Cy-R^2$,
$R^1-Z^1-A-Z^2-Phe-Phe-Phe-R^2$,
$R^1-Z^1-A-Z^2-Phe-Phe-Cy-R^2$,
$R^1-Z^1-A-R^2-Phe-Cy-Phe-R^2$,
$R^1-Z^1-A-Z^2-Phe-Cy-Cy-R^2$,
$R^1-Z^1-A-Z^2-Cy-Phe-Phe-R^2$,
$R^1-Z^1-A-Z^2-Cy-Phe-R^2$,
$R^1-Z^1-A-Z^2-Cy-Cy-Phe-R^2$, or
$R^1-Z^1-A-Z^2-Cy-Cy-Cy-R^2$
wherein "A" is 1,4-dioxane-2,5-diyl, "Phe" is 1,4-phenylene, "Cy" is 1,4-cyclohexylene, "Dio" is 1,3-dioxane-2,5-diyl, "Bi" is bicyclo(2,2,2)-octylene, "Pip" is piperidine-1,4-diyl and "Pyr" is pyrimidine-2,5-diyl.

10. A liquid-crystalline dielectric of claim 9 of the formula
$R^1-Z^1-A-Z^2-Phe-Phe-R^2$, or
$R^1-Z^1-A-Z^2-Phe-Phe-Cy-R^2$.

11. A liquid-crystalline dielectric of claim 1 wherein $R^1$ and $R^2$ are alkyl.

12. A liquid-crystalline dielectric of claim 1 wherein $A^1$ and $A^2$ are Cy or Phe wherein Cy is 1,4-cyclohexylene and Phe is 1,4-phenylene.

13. A liquid-crystalline dielectric of claim 1, wherein $Z^1$ and $Z^2$ are single bonds, -CO-O- or -O-CO-.

14. A liquid-crystalline dielectric of claim 1 wherein m is 0 and n is 1.

15. A liquid-crystalline dielectric of claim 1 of the formula
$R^1-A-Z^2-A^2-R^2$,
$R^1-A-A^2-R^2$,
$R^1-A-Phe-R^2$,
$R^1-A-Phe-CN$,
$R^1-A-(A^2)_2-R^2$,
$R^1-A-Phe-Phe-R^2$,
$R^1-A-(A^2)_3-R^2$, or
$R^1-A-Phe-Phe-Cy-R^2$
wherein "A" is 1,4-dioxane-2,5-diyl, "Phe" is 1,4-phenylene and "Cy" 1,4-cyclohexylene.

16. A liquid-crystalline dielectric of claim 1 comprising 2-20 liquid-crystalline components.

17. In an electro-optical cell comprising a liquid-crystalline dielectric, the improvement wherein the dielectric is one of claim 1.

18. A liquid-crystalline dielectric of claim 1 wherein the compound is trans-2-p-ethoxyphenyl-5-pentyl-1,4-dioxane.

19. A liquid-crystalline dielectric of claim 1 wherein $A^1$ or $A^2$ is 1,4-dioxane-2,5-diyl, piperidine-1,4-diyl, 1,4-bicyclo(2,2,2)-octylene or pyrimidine-2,5-diyl, or is substituted by 1-4 F atoms.

20. A liquid-crystalline dielectric useful in an electro-optical indicator element and comprising at least two liquid-crystalline compounds, wherein at least one such component is a compound of the formula

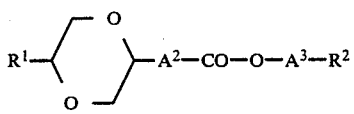

wherein
R¹ and R² each independently is alkyl of 1–10 C-atoms, F, Cl, Br, CN or alkyl of 1–10 C-atoms wherein one or two non-adjacent CH₂ groups are replaced by O atoms, R² can also be H, A² is 1,4-phenylene, unsubstituted or substituted by 1–4 F-atoms, and A³ is 1,4-phenylene, 1,4-cyclohexylene, 1,3-dioxane-2,5-diyl, 1,4-dioxane-2,5-diyl, piperidine-1,4-diyl, 1,4-bicyclo(2,2,2)-octylene or pyrimidine-2,5-diyl, unsubstituted or substituted by 1–4 F-atoms.

* * * * *